United States Patent [19]

Bowen et al.

[11] Patent Number: 5,147,322

[45] Date of Patent: Sep. 15, 1992

[54] MEDICAL APPLIANCE SECURING DEVICE

[75] Inventors: Michael L. Bowen, Arlington; Roger A. Liebelt, Mansfield, both of Tex.

[73] Assignee: Highpoint Medical Corporation, Arlington, Tex.

[21] Appl. No.: 799,122

[22] Filed: Nov. 26, 1991

[51] Int. Cl.⁵ ............................................ A61M 25/02
[52] U.S. Cl. ............................ 604/180; 128/DIG. 26
[58] Field of Search ....................... 604/174, 179, 180; 128/DIG. 26

[56] References Cited

U.S. PATENT DOCUMENTS

| | | | |
|---|---|---|---|
| 3,160,158 | 12/1964 | Rayhart | 128/349 |
| 3,288,136 | 11/1966 | Lund | 128/133 |
| 3,430,300 | 3/1969 | Doan | 24/73 |
| 3,677,250 | 7/1972 | Thomas | 128/348 |
| 3,726,280 | 4/1973 | Lacount | 128/349 R |
| 3,765,421 | 10/1973 | Poprik | 128/349 R |
| 3,782,383 | 1/1974 | Thompson et al. | 128/214 |
| 3,826,254 | 7/1974 | Mellor | 128/133 |
| 3,834,380 | 9/1974 | Boyd | 604/180 |
| 3,878,849 | 4/1975 | Muller et al. | 128/349 R |
| 3,990,454 | 11/1976 | Schlesinger | 128/349 R |
| 4,096,863 | 6/1978 | Kaplan et al. | 128/DIG. 26 |
| 4,122,857 | 10/1978 | Haerr | 604/180 |
| 4,165,748 | 8/1979 | Johnson | 128/348 |
| 4,333,468 | 6/1982 | Geist | 604/180 |
| 4,336,806 | 6/1982 | Eldridge, Jr. | 128/348 |
| 4,378,012 | 3/1983 | Brown | 128/207.17 |
| 4,416,664 | 11/1983 | Womack | 604/174 |
| 4,445,894 | 5/1984 | Kovacs | 604/179 |
| 4,447,238 | 5/1984 | Eldridge, Jr. | 604/280 |
| 4,569,348 | 2/1986 | Hasslinger | 128/DIG. 26 |
| 4,571,245 | 2/1986 | Hubbard et al. | 604/179 |
| 4,583,976 | 4/1986 | Ferguson | 604/174 |
| 4,591,356 | 5/1986 | Christie | 604/179 |
| 4,617,017 | 10/1986 | Hubbard et al. | 128/DIG. 26 |
| 4,700,432 | 10/1987 | Fennell | 128/DIG. 26 |
| 4,702,736 | 10/1987 | Kalt et al. | 604/180 |
| 4,726,716 | 2/1988 | McGuire | 604/174 |
| 4,838,868 | 6/1989 | Forgar et al. | 604/180 |
| 4,854,015 | 8/1989 | Shaull | 24/16 R |
| 4,874,380 | 10/1989 | Hesketh | 604/180 |
| 4,898,587 | 2/1990 | Mera | 604/174 |
| 4,919,654 | 4/1990 | Kalt | 604/180 |
| 4,962,757 | 10/1990 | Stefan | 128/DIG. 26 |
| 4,966,590 | 10/1990 | Kalt | 604/180 |
| 4,976,700 | 12/1990 | Tollini | 604/180 |
| 5,019,050 | 5/1991 | Lynn et al. | 604/179 |
| 5,073,170 | 12/1991 | Schneider | 128/DIG. 26 |

Primary Examiner—Paul J. Hirsch
Attorney, Agent, or Firm—Richards, Medlock & Andrews

[57] ABSTRACT

A medical appliance securing device for laterally and longitudinally securing generally tubular members having various diameters to any desired location on the surface of a patient's skin or other support. The invention comprises an anchoring patch having one surface coated with adhesive for bonding the device to a patient's skin or some other support. A retaining tab is connected to the anchoring patch and contains an aperture such that the retaining tab may be wrapped around the circumference of the tubular member, inserted through the aperture, and firmly secured to the anchoring patch through the use of fastening means.

7 Claims, 1 Drawing Sheet

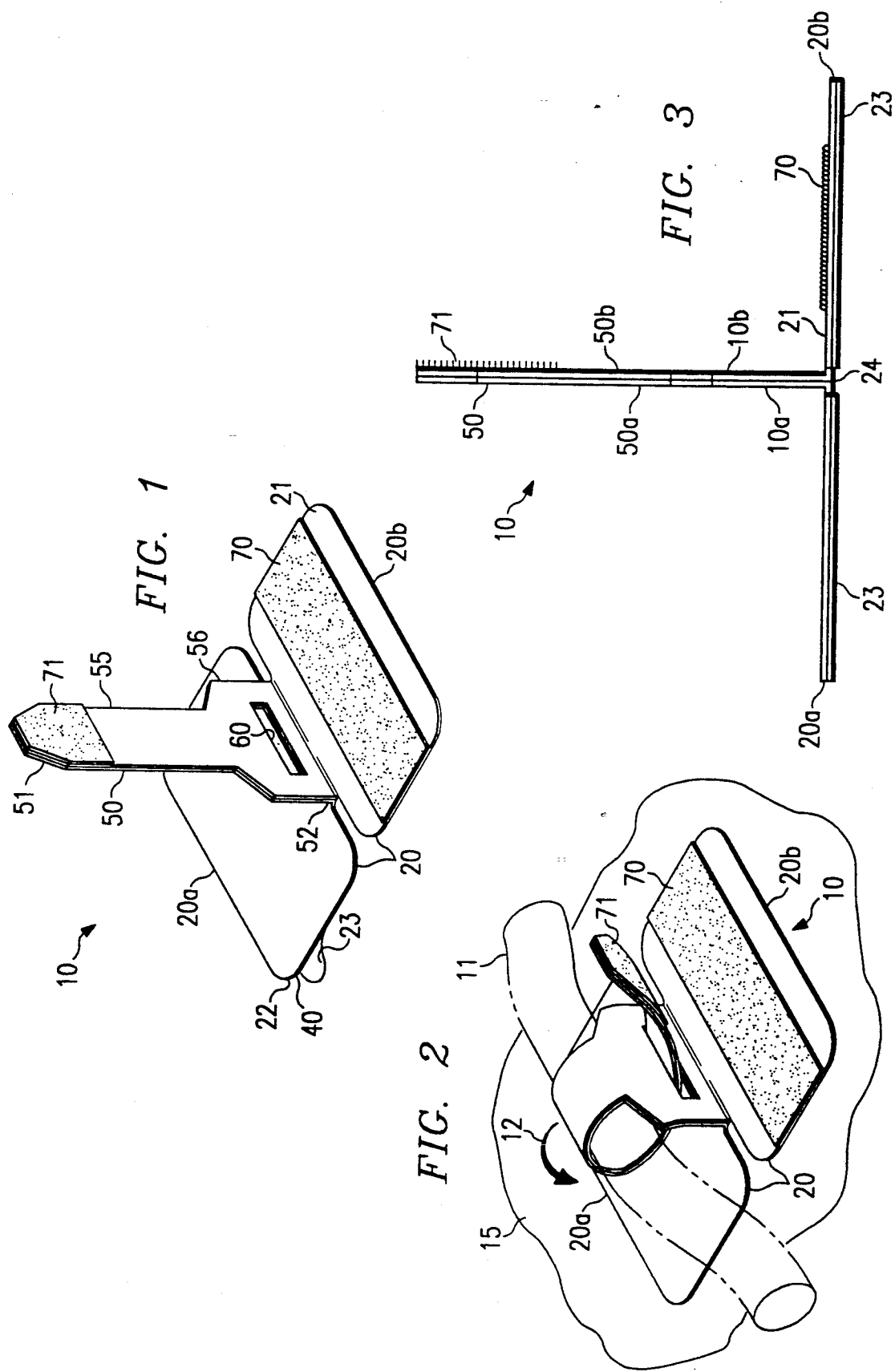

MEDICAL APPLIANCE SECURING DEVICE

TECHNICAL FIELD OF THE INVENTION

This invention relates in general to devices useful for securing medical appliances to surfaces, and more particularly, to devices useful for laterally, longitudinally, and removably securing tubes, rods, cords, wires or leads of various diameters to a patient's skin or to some other support surface.

BACKGROUND OF THE INVENTION

Various medical devices, or portions thereof, are shaped as generally tubular members, such as, for example, catheters, thermometers, i.v. tubing and various types of electrical wires. Many times there is a need to secure the device to or near the patient's body so that the device can appropriately function. In particular, catheters are medical appliances often used in surgical procedures for transporting various types of fluids to and from the body of the patient. These devices are generally long, tubular conduits made from flexible materials and extend from the patient to a nearby, stationary receptacle or source of fluid. Therefore, it is often necessary to secure the medical appliance tube near its insertion point on the patient's body to insure proper placement and functioning of the catheter, as well as to offer some degree of comfort and mobility for the patient. In addition, some medical procedures require the application of a tensile force, known as traction, to the catheter, thus making it particularly necessary to firmly secure the catheter tube in its longitudinal direction.

To provide the necessary restraint, practitioners initially used strips of conventional, medical-grade adhesive tape to secure the catheter tube directly to the patient's skin. This method proved unsuccessful, however, because the tape would tend to become loose, and because each time the catheter was adjusted or temporarily removed it was necessary to also remove the adhesive tape from the patient's skin, thus causing significant irritation and discomfort.

Various types of catheter securing devices were subsequently developed to provide the desired restraint and overcome the disadvantages associated with the use of strips of adhesive tape. For example, U.S. Pat. Nos. 4,096,863; 4,571,245; and 4,617,017 each disclose catheter securing devices comprising a strap which encircles the limb of the patient. The disadvantage of such devices lies in the fact that in order to adequately restrain the catheter tube, the strap must be kept fairly tight, which can cause discomfort and restrict blood flow to the patient's limb. Furthermore, since the strap can only be applied to a limb, the practitioner is limited as to the number and type of locations to which the catheter tube may be secured.

U.S. Pat. Nos. 4,165,748 and 4,976,700 disclose a second type of catheter securing device comprising a segment of material having one side coated with adhesive which is designed to be applied directly to the patient's skin. A central tab extends from the segment of material and has fastening means for securing the catheter tube. A disadvantage associated with these devices is the fact that they function properly only for particular catheter tube sizes. Hospitals are therefore required to stock different sizes of securing devices in order to accommodate different catheter tube diameters. In addition, these devices suffer from an inability to adequately restrain the catheter tube in its longitudinal direction.

A need therefore exists for an inexpensive medical appliance securing device which may be positioned anywhere on a patient's skin or other support and which will reliably secure various diameters of catheter tubes or other generally tubular members in both the longitudinal and lateral directions.

SUMMARY OF THE INVENTION

The invention disclosed and claimed herein is an improved medical appliance securing device comprising an anchoring patch having one surface coated with adhesive for attaching the device at any desired location on the patient's skin or other support surface. A retaining tab extends from the anchoring patch. The retaining tab has a narrow portion near its free end and a wide portion having an aperture near its connected end. Fastening means are located on the free end of the retaining tab. Complementary fastening means are located at the top surface of the anchoring patch. A preferred fastening means is hook and pile material. In operation, the narrow portion of the retaining tab is wrapped around the tubular member and is then passed through the aperture in the wide portion of the retaining tab. The free end of the retaining tab is then pulled so that the retaining tab tightens around the tubular member, firmly gripping the object about its circumference. The grip is maintained by attaching the fastening means on the free end of the retaining tab to the complementary fastening means on the top surface of the anchoring patch.

Because of the use of the retaining tab in conjunction with the use of the anchoring patch, the present invention may be attached anywhere on the patient's skin or other support. The practitioner is not limited to placing the device on the patient's limb, nor is the practitioner limited to placing the device at a particular location on the tubular member. The anchoring patch may also be attached to the surface of a table or other device near the patient. Furthermore, the design of the retaining tab allows the application of traction to the catheter and allows the device to be used to restrain various diameters of catheter tubes or other tubular members, thus making it unnecessary for hospitals to stock numerous sizes of catheter securing devices.

BRIEF DESCRIPTION OF THE DRAWINGS

A more complete understanding of the present invention and its advantages will be apparent from the following Detailed Description taken in conjunction with the accompanying drawings, in which:

FIG. 1 is a perspective view of the present invention as it is ready for use.

FIG. 2 is a perspective view of the present invention as it is used to secure a catheter tube (shown in phantom) to a surface.

FIG. 3 is a side elevational view showing details of the construction of the present invention.

DETAILED DESCRIPTION

A tube holder in accordance with the preferred embodiment of the present invention is indicated generally at 10 of FIG. 1. Anchoring patch 20 comprises a first segment 20a and a second segment 20b and has a top surface 21 and a bottom surface 22. First segment 20a and second segment 20b are connected along inner edge 24 (FIG. 3). Pressure-sensitive adhesive 40 covers bottom surface 22 of anchoring patch 20 causing release liner 23 to adhere to bottom surface 22. Release liner 23 may be peeled off to expose adhesive 40 on bottom surface 22 for bonding tube holder 10 to a surface 15 (FIG. 2) of a patient's skin or other support.

Retaining tab 50 extends from anchoring patch 20 and has a free end 51 and a connected end 52, which is integrally attached to anchoring patch 20. Retaining tab 50 also has a narrow portion 55 near free end 51 and a wide portion 56 near connected end 52. Wide portion 56 additionally has an aperture 60. Narrow portion 55 and aperture 60 of retaining tab 50 are dimensioned such that narrow portion 55 may be wrapped around the circumference of a tubular member, inserted through aperture 60, and extended far enough past aperture 60 to contact top surface 21 of anchoring patch 20.

A first fastening means 70 is located on top surface 21 of anchoring patch 20, and a second complementary fastening means 71 is located at free end 51 on the side of retaining tab 50 facing the first fastening means 70 on top surface 21. A preferred fastening means is hook or pile fastening material, such as the material sold under the trademark "VELCRO." Another preferred fastening means is resealable adhesive tape. In addition, it will be understood by those skilled in the art that any other fastening material which allows repeated fastening and unfastening and which allows the connection to be made at various positions will be suitable.

In use, release liner 23 is peeled away from anchoring patch 20, thereby exposing bottom surface 22 coated with adhesive 40. As best seen in FIG. 2, the anchoring patch 20 is then pressed against the desired location on surface 15 of the patient's skin or other support, with the adhesive 40 thereby securely bonding anchoring patch 20 to surface 15. A tubular member 11, shown in phantom in FIG. 2, is then positioned so that it extends across tube holder 10 and alongside retaining tab 50. Retaining tab 50 is next wrapped about tubular member 11 in the direction of arrow 12, and the narrow portion 55 of retaining tab 50 is inserted through aperture 60, so that retaining tab 50 makes a substantially complete revolution about the circumference of tubular member 11. The free end 51 of retaining tab 50 is then pulled tight and pressed down upon top surface 21, causing the first fastening means 70 to become engaged with the complementary second fastening means 71 and thus securely and removably fastening the free end 51 of retaining tab 50 to top surface 21.

The firm grip exerted by retaining tab 50 upon the circumference of tubular member 11 restrains movement of tubular member 11 in its lateral and longitudinal directions. Furthermore, because the first fastening means 70 and the complementary second fastening means 71 may be repeatedly connected and disconnected without losing their fastening ability, tubular member 11 may be repeatedly removed and resecured without the tube holder 10 losing its ability to firmly and reliably restrain the tubular member 11. Tubular member 11 is removed by simply pulling upward on the free end 51 of retaining tab 50, thereby causing the first fastening means 70 and the complementary second fastening means 71 to disconnect, removing narrow portion 55 of retaining tab 50 from aperture 60, and unwrapping retaining tab 50 from around tubular member 11.

As best seen in FIG. 3, the preferred embodiment of tube holder 10 is constructed from a first piece 10a and a second piece 10b which have been die cut from a sheet of medical-grade material, such as the material sold under the trademark "DURAPORE." Those skilled in the art will understand, however, that any other material suitable for similar medical applications may be used. First piece 10a comprises first segment 20a of anchoring patch 20 and retaining tab element 50a. Second piece 10b comprises second segment 20b of anchoring patch 20 and retaining tab element 50b. First piece 10a and second piece 10b each have one surface coated with pressure-sensitive adhesive.

Tube holder 10 is formed by aligning and joining the adhesive-coated surfaces of retaining tab elements 50a and 50b, thus causing first piece 10a to adhere to second piece 10b. Release liner 23 is then applied to the adhesive-coated surface of first segment 20a and second segment 20b of anchoring patch 20. First fastening means 70 is next adhesively bonded to top surface 21 of anchoring patch 20, and complementary second fastening means 71 is adhesively bonded to narrow portion 55 of retaining tab 50, on the side of retaining tab 50 facing first fastening means 70. As a final step, aperture 60 is die cut in wide portion 56 of retaining tab 50.

Alternatively, tube holder 10 may be constructed from two separate sheets of medical-grade material. Under this method, portions of the two sheets are first adhesively joined, and release liner 23 is laminated to the remaining portions of the sheets, thus creating a workpiece having a generally T-shaped cross section. First fastening means 70 and complementary second fastening means 71 are then adhesively bonded to the workpiece. Finally, tube holder 10 is die cut as a finished unit from the workpiece.

It will be understood by those skilled in the art that the design of retaining tab 50 allows tube holder 10 to be used to secure tubular members having various diameters. This versatility is possible because once retaining tab 50 has been wrapped around tubular member 11 and narrow portion 55 has been inserted through aperture 60, tubular member 11 is gripped by pulling on free end 51 until retaining tab 50 tightens around the circumference of tubular member 11. To accommodate different diameters of tubular member 11 it is only necessary to pull narrow portion 55 through aperture 60 by the amount necessary to firmly grip the particular tubular member 11.

It will additionally be understood by those skilled in the art that tube holder 10 allows the application of traction to tubular member 11. Because of the firm grip applied by retaining tab 50, tubular member 11 is restrained in its longitudinal direction, thus supporting a traction force.

Finally, it will be understood that anchoring patch 20 and retaining tab 50 allow the practitioner great flexibility in positioning tube holder 10. Anchoring patch 20 allows the device to be attached virtually anywhere on the patient's skin or other support, not just on a patient's limb as with the prior art strap devices. Because retaining tab 50 may be applied to numerous sizes of tubular member 11, the practitioner is not limited to placing retaining tab 50 of tube holder 10 at a particular location on tubular member 11, as with the prior art tape devices.

Although the preferred embodiment of the invention has been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit and scope of the invention. For example, it will be understood by those skilled in the art that the structure as described may be made larger or smaller in size and may be made of materials other than those described. In addition, although the use of an anchoring patch having two segments is disclosed, those skilled in the art will understand that the present invention will perform its function of securing tubular members with only one anchoring patch segment. The present invention is therefore intended to encompass such rearrangements, modifications, and substitutions of parts and elements.

We claim:

1. A holder for securing a generally tubular member of a medical device to a support surface comprising:

an anchoring patch having a top surface and a bottom surface, said bottom surface coated with an adhesive for attaching said anchoring patch to the support surface;

a retaining tab having a first portion and a second portion, said first portion connected to said anchoring patch and having an aperture therein, said second portion having a width less than the width of said first portion and dimensioned to allow said second portion to be inserted through said aperture, said retaining tab being of sufficient length to wrap around the circumference of the generally tubular member, extend through said aperture and contact said top surface of said anchoring patch; and first fastening means secured to said top surface of said anchoring patch and complementary second fastening means secured to said second portion of said retaining tab such that when said retaining tab is wrapped around the circumference of the generally tubular member and said second portion of said retaining tab is inserted through said aperture, said first fastening means may be firmly and removably secured to said complementary fastening means.

2. The holder of claim 1 wherein said anchoring patch comprises a first segment having an inner edge and a second segment connected to said first segment along said inner edge.

3. The holder of claim 2 wherein said first portion of said retaining tab is connected to said first segment and said second segment of said anchoring patch along said inner edge.

4. The holder of claim 1 wherein said first fastening means is hook or pile fastening material and said complementary second fastening means is complementary hook or pile fastening material.

5. The holder of claim 1 wherein said first fastening means and said complementary second fastening means are resealable adhesive tape.

6. A holder for securing a generally tubular member of a medical device to a support surface comprising:

an anchoring patch comprising a first segment and a second segment, said first segment having an inner edge and said second segment being connected to said first segment along said inner edge, said anchoring patch having a top surface and a bottom surface, said bottom surface coated with an adhesive for attaching said anchoring patch to the support surface;

a retaining tab having a free end and a connected end, said connected end attached to said anchoring patch along said inner edge and integral with said first segment and said second segment of said anchoring patch, said retaining tab comprising a wide portion near said connected end and a narrow portion near said free end, said wide portion having an aperture therein dimensioned to allow the insertion of said narrow portion, said retaining tab having a length sufficient to wrap around the circumference of the generally tubular member, extend through said aperture, and contact said top surface of said anchoring patch; and hook or pile fastening material adhesively bonded to said top surface of said second segment of said anchoring patch and complementary hook or pile fastening material adhesively bonded to said narrow portion of said retaining tab on the side of said retaining tab facing said second segment of said anchoring patch.

7. A holder for securing a generally tubular member of a medical device to a support surface comprising:

an anchoring patch comprising a first segment and a second segment, said first segment having an inner edge and said second segment being connected to said first segment along said inner edge, said anchoring patch having a top surface and a bottom surface, said bottom surface coated with an adhesive for attaching said anchoring patch to the support surface;

a retaining tab having a free end and a connected end, said connected end attached to said anchoring patch along said inner edge and integral with said first segment and said second segment of said anchoring patch, said retaining tab comprising a wide portion near said connected end and a narrow portion near said free end, said wide portion having an aperture therein dimensioned to allow the insertion of said narrow portion, said retaining tab having a length sufficient to wrap around the circumference of the generally tubular member, extend through said aperture, and contact said top surface of said anchoring patch; and resealable adhesive tape secured to said top surface of said second segment of said anchoring patch and complementary resealable adhesive tape secured to said narrow portion of said retaining tab on the side of said retaining tab facing said second segment or said anchoring patch.

* * * * *

REEXAMINATION CERTIFICATE (2767th)

United States Patent [19]
Bowen et al.

[11] B1 5,147,322
[45] Certificate Issued Jan. 2, 1996

[54] MEDICAL APPLIANCE SECURING DEVICE

[75] Inventors: Michael L. Bowen, Arlington; Roger A. Liebelt, Mansfield, both of Tex.

[73] Assignee: TCNL Technologies, Inc., Wilmington, Del.

Reexamination Request:
No. 90/003,578, Sep. 19, 1994

Reexamination Certificate for:
Patent No.: 5,147,322
Issued: Sep. 15, 1992
Appl. No.: 799,122
Filed: Nov. 26, 1991

[51] Int. Cl.⁶ .................................................. A61M 25/02
[52] U.S. Cl. ................................. 604/180; 128/DIG. 26
[58] Field of Search .................................... 604/174, 179, 604/180; 128/DIG. 26

[56] References Cited

U.S. PATENT DOCUMENTS

| | | | |
|---|---|---|---|
| 4,096,863 | 6/1978 | Kaplan et al. | 128/DIG. 26 |
| 4,571,245 | 2/1986 | Hubbard et al. | 128/DIG. 26 |
| 4,604,091 | 8/1986 | Billarant et al. | 604/180 |
| 4,617,017 | 10/1986 | Hubbard et al. | 604/179 |

*Primary Examiner*—Paul J. Hirsch

[57] ABSTRACT

A medical appliance securing device for laterally and longitudinally securing generally tubular members having various diameters to any desired location on the surface of a patient's skin or other support. The invention comprises an anchoring patch having one surface coated with adhesive for bonding the device to a patient's skin or some other support. A retaining tab is connected to the anchoring patch and contains an aperture such that the retaining tab may be wrapped around the circumference of the tubular member, inserted through the aperture, and firmly secured to the anchoring patch through the use of fastening means.

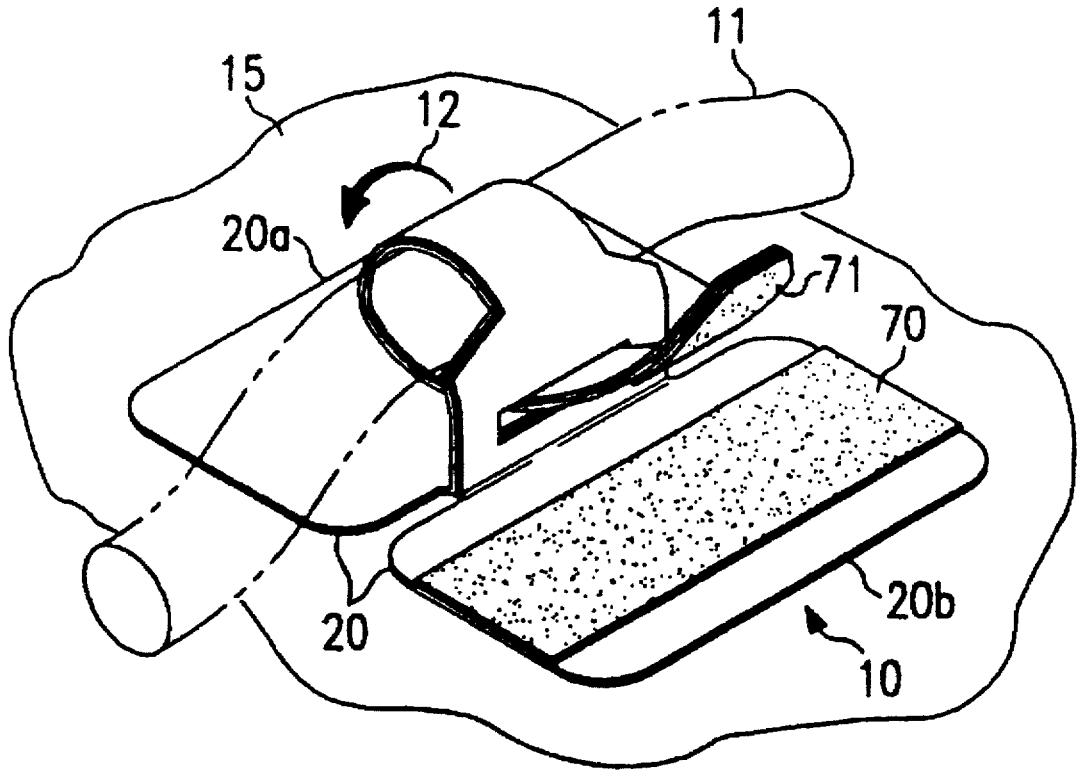

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 6–7 is confirmed.

Claim 1 is determined to be patentable as amended.

Claims 2–5, dependent on an amended claim, are determined to be patentable.

1. A holder for securing a generally tubular member of a medical device to a support surface comprising:

an anchoring patch having a top surface and a bottom surface, said bottom surface coated with an adhesive for attaching said anchoring patch to the support surface;

a retaining tab having a first portion and a second portion, said first portion *non-removably* connected to said anchoring patch and having an aperture therein, said second portion having a width less than the width of said first portion and dimensioned to allow said second portion to be inserted through said aperture, said retaining tab being of sufficient length to wrap around the circumference of the generally tubular member, extend through said aperture and contact said top surface of said anchoring patch; and first fastening means secured to said top surface of said anchoring patch and complementary second fastening means secured to said second portion of said retaining tab such that when said retaining tab is wrapped around the circumference of the generally tubular member and said second portion of said retaining tab is inserted through said aperture, said first fastening means may be firmly and removably secured to said complementary fastening means.

* * * * *